(12) United States Patent
Rosenberg et al.

(10) Patent No.: US 9,949,666 B2
(45) Date of Patent: Apr. 24, 2018

(54) METHOD AND SYSTEM FOR DETERMINING A DEVICE MOVEMENT IRRESPECTIVE OF MOVEMENT OF A REFERENCE FRAME

(71) Applicant: GIVEN IMAGING LTD., Yoqneam (IL)

(72) Inventors: Oren Rosenberg, Kiryat Ono (IL); Semion Khait, Tiberias (IL)

(73) Assignee: GIVEN IMAGING LTD., Yoqneam (IL)

( * ) Notice: Subject to any disclaimer, the term of this patent is extended or adjusted under 35 U.S.C. 154(b) by 334 days.

(21) Appl. No.: 14/761,320

(22) PCT Filed: Feb. 6, 2014

(86) PCT No.: PCT/IL2014/050133
§ 371 (c)(1),
(2) Date: Jul. 16, 2015

(87) PCT Pub. No.: WO2014/122655
PCT Pub. Date: Aug. 14, 2014

(65) Prior Publication Data
US 2015/0335264 A1    Nov. 26, 2015

Related U.S. Application Data

(60) Provisional application No. 61/762,401, filed on Feb. 8, 2013.

(51) Int. Cl.
*A61B 5/06*    (2006.01)
*A61B 1/045*    (2006.01)
(Continued)

(52) U.S. Cl.
CPC ............ *A61B 5/067* (2013.01); *A61B 1/0002* (2013.01); *A61B 1/00006* (2013.01);
(Continued)

(58) Field of Classification Search
CPC ..... A61B 5/067; A61B 1/045; A61B 1/00006; A61B 1/0002; A61B 1/041; A61B 5/073;
(Continued)

(56) References Cited

U.S. PATENT DOCUMENTS 6,709,387 B1    3/2004    Glukhovsky et al.
6,944,316 B2    9/2005    Glukhovsky et al.
(Continued)

FOREIGN PATENT DOCUMENTS

CN    101674769    3/2010
CN    102006825    4/2011
(Continued)

*Primary Examiner* — Navin Natnithithadha
(74) *Attorney, Agent, or Firm* — Pearl Cohen Zedek Latzer Baratz LLP

(57) ABSTRACT

A swallowable in-vivo device contains a movement detection unit that includes a movement sensing unit, a frequency analyzing unit (FAU) and a time analyzing unit (TAU). The movement sensing unit senses movements of the in-vivo device relative to a non-stationary three-dimensional reference frame, and outputs a movement signal. The frequency analyzing unit may analyze the movement signal spectrally to detect a potential command-invoking movement, and the time analyzing unit may analyze the potential CIM temporally, possibly in conjunction with a series of other movement events, to determine whether the potential CIM is a genuine CIM. If the potential CIM is determined to be a genuine CIM, the in-vivo device may execute a predetermined command associated with the CIM. Otherwise, the in-vivo device may refrain from executing a CIM-related command. A PCB including the movement detection unit and a processor for processing their output is provided for the vivo sensing device.

18 Claims, 8 Drawing Sheets

(51) Int. Cl.
*A61B 1/04* (2006.01)
*A61B 5/07* (2006.01)
*A61B 5/11* (2006.01)
*A61B 5/00* (2006.01)
*A61B 1/00* (2006.01)

(52) U.S. Cl.
CPC .............. *A61B 1/041* (2013.01); *A61B 1/045* (2013.01); *A61B 5/073* (2013.01); *A61B 5/1107* (2013.01); *A61B 5/1123* (2013.01); *A61B 5/7282* (2013.01); *A61B 5/7475* (2013.01); *A61B 2562/0219* (2013.01); *A61B 2562/166* (2013.01); *A61B 2562/227* (2013.01)

(58) Field of Classification Search
CPC ... A61B 5/1107; A61B 5/1123; A61B 5/7282; A61B 5/7475; A61B 2562/0219; A61B 2562/166; A61B 2562/227; A61B 1/00; A61B 1/04; A61B 1/05; A61B 1/273; A61B 1/147; A61B 1/156; A61B 1/051
USPC ........ 600/302, 101, 109, 118, 160, 593, 921
See application file for complete search history.

(56) References Cited

U.S. PATENT DOCUMENTS

| | | | | |
|---|---|---|---|---|
| 8,162,821 B2* | 4/2012 | Kawano | ............ | A61B 1/00016 128/899 |
| 8,632,459 B2* | 1/2014 | Aoki | ................. | A61B 1/00156 600/117 |
| 8,790,247 B2* | 7/2014 | Kawano | ............ | A61B 1/00016 600/114 |
| 8,965,079 B1 | 2/2015 | Zinaty et al. | | |
| 9,198,563 B2* | 12/2015 | Ferren | ................... | A61B 1/041 |
| 9,408,530 B2* | 8/2016 | Ferren | ................... | A61B 1/041 |
| 2005/0065441 A1 | 3/2005 | Glukhovsky | | |
| 2007/0221233 A1* | 9/2007 | Kawano | ............ | A61B 1/00016 128/899 |
| 2008/0300453 A1* | 12/2008 | Aoki | ................. | A61B 1/00156 600/103 |
| 2010/0130818 A1 | 5/2010 | Jung et al. | | |
| 2010/0150416 A1 | 6/2010 | Kim et al. | | |
| 2010/0326703 A1 | 12/2010 | Gilad et al. | | |
| 2012/0035434 A1* | 2/2012 | Ferren | ................ | A61B 1/00156 600/301 |
| 2012/0035437 A1* | 2/2012 | Ferren | ................... | A61B 1/041 600/302 |
| 2012/0035438 A1* | 2/2012 | Ferren | ................... | A61B 1/041 600/302 |
| 2012/0035439 A1* | 2/2012 | Ferren | ................... | A61B 1/041 600/302 |
| 2012/0035440 A1* | 2/2012 | Ferren | ................... | A61B 1/041 600/302 |
| 2012/0035540 A1* | 2/2012 | Ferren | ................... | A61B 1/041 604/95.01 |
| 2012/0041291 A1* | 2/2012 | Ferren | ................... | A61B 1/041 600/365 |
| 2012/0200684 A1 | 8/2012 | Glukhovsky et al. | | |
| 2012/0265015 A1* | 10/2012 | Kawano | ............ | A61B 1/00016 600/118 |
| 2014/0031642 A1 | 1/2014 | Kimchy et al. | | |

FOREIGN PATENT DOCUMENTS

| | | |
|---|---|---|
| CN | 102802499 | 11/2012 |
| EP | 1714607 | 10/2006 |
| JP | 2004521662 | 7/2004 |
| JP | 2006297109 | 11/2006 |
| JP | 2009195271 | 9/2009 |
| WO | WO2012/056323 | 5/2012 |

* cited by examiner

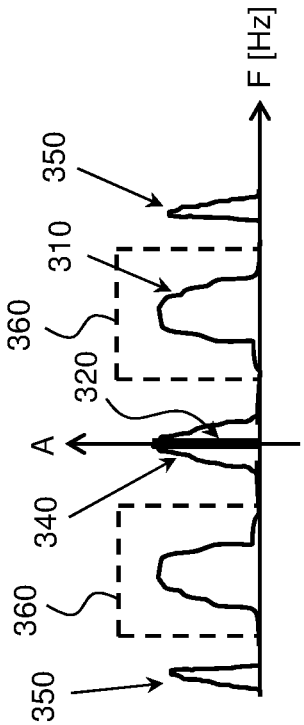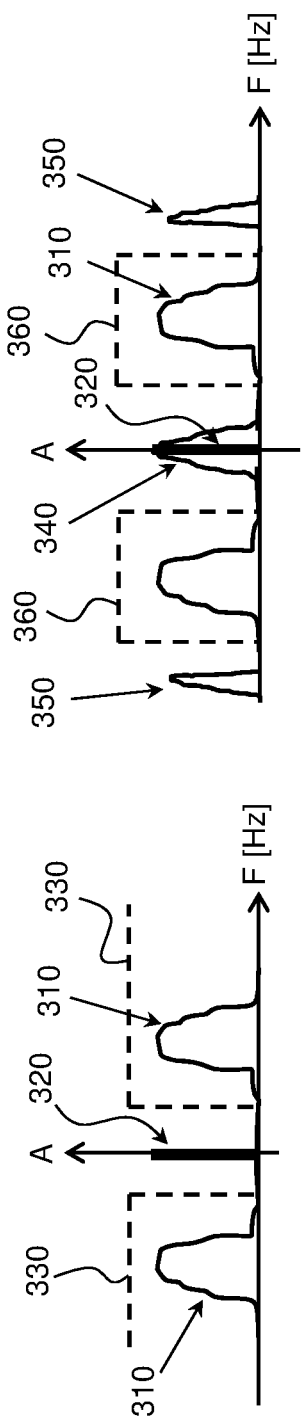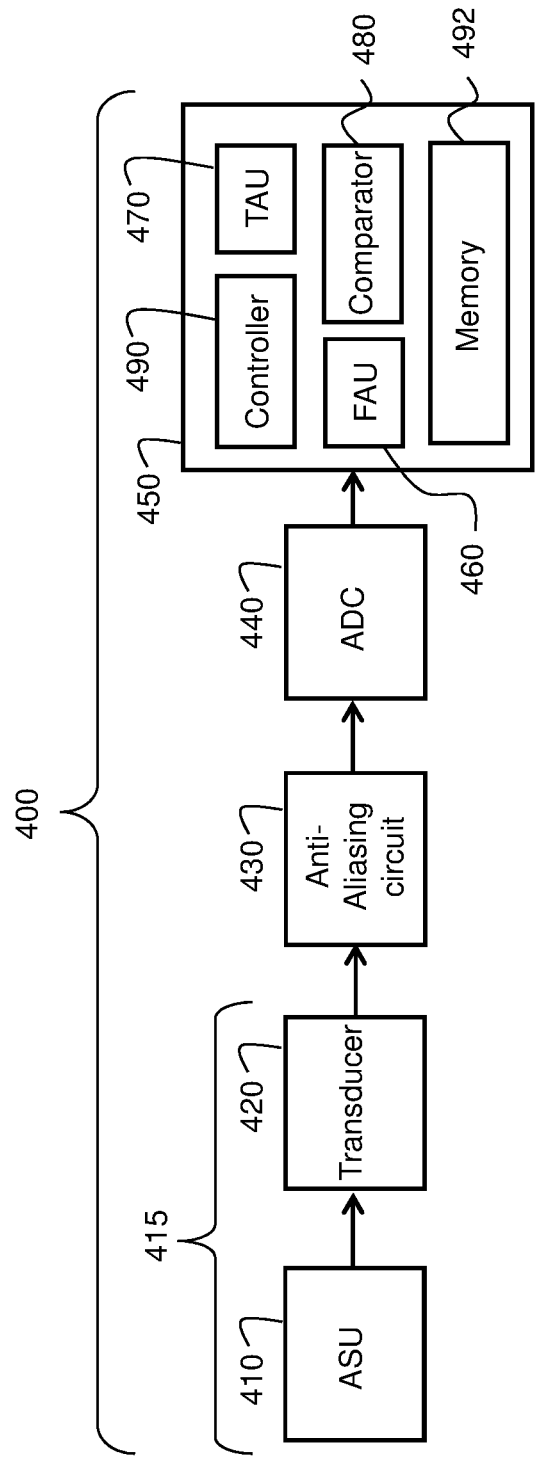

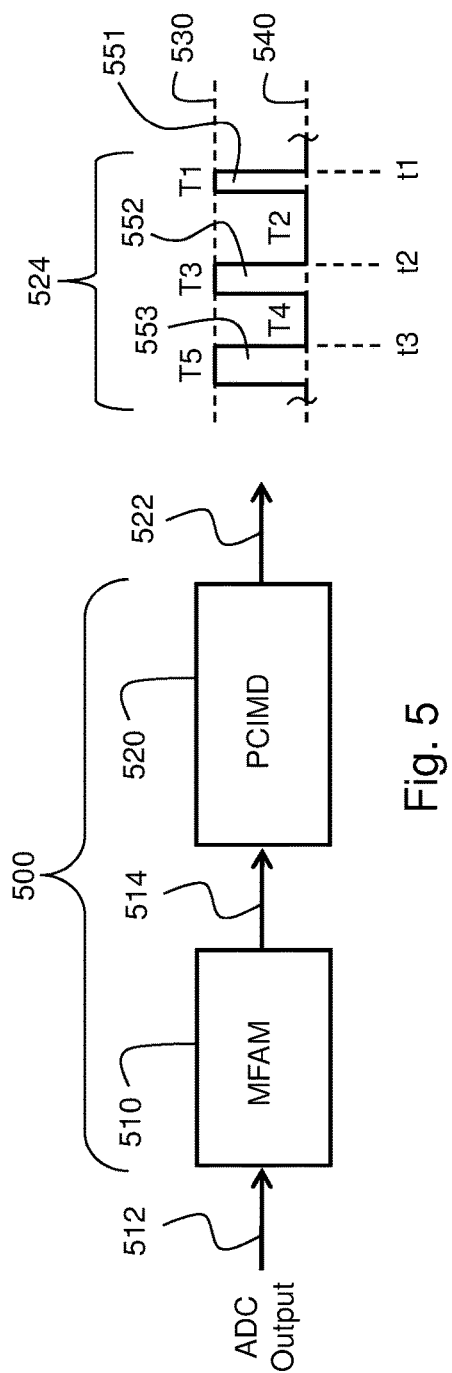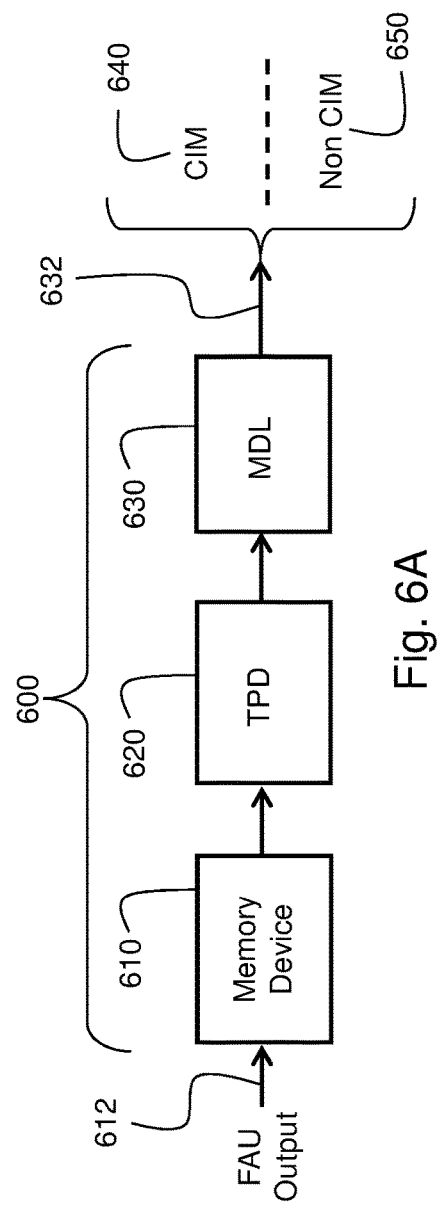
Fig. 5
Fig. 6A

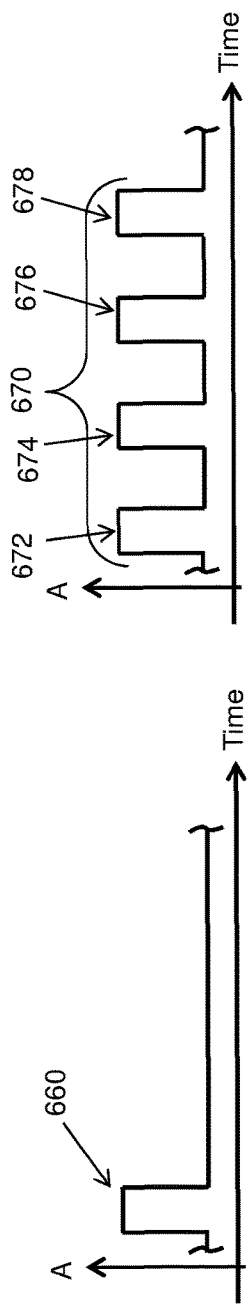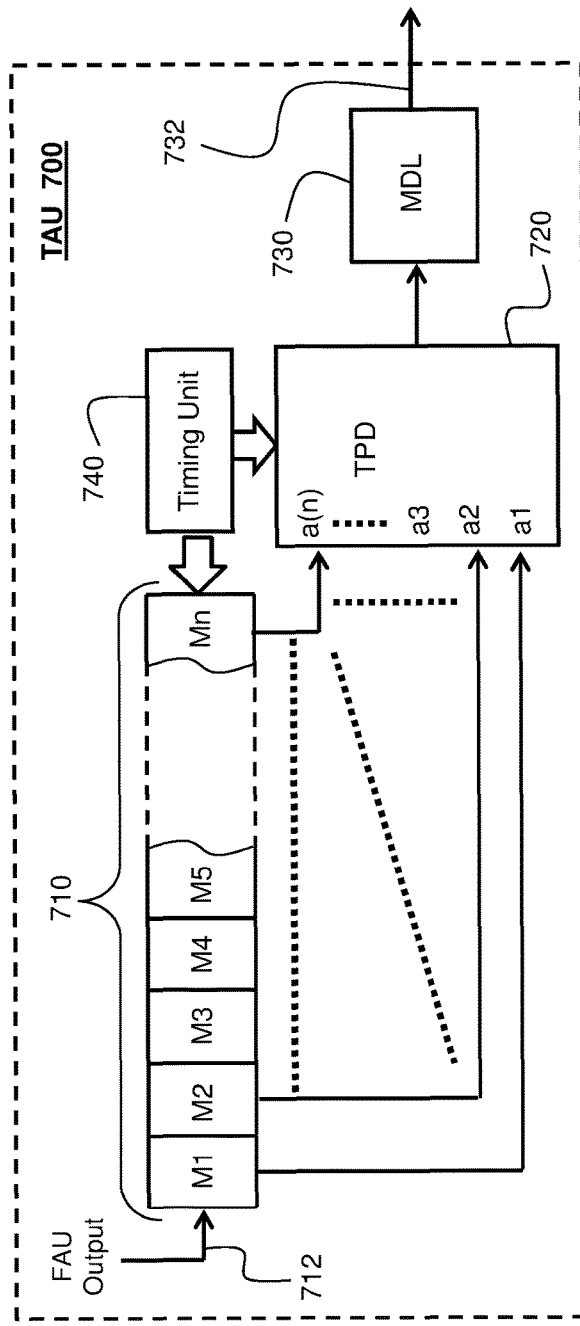

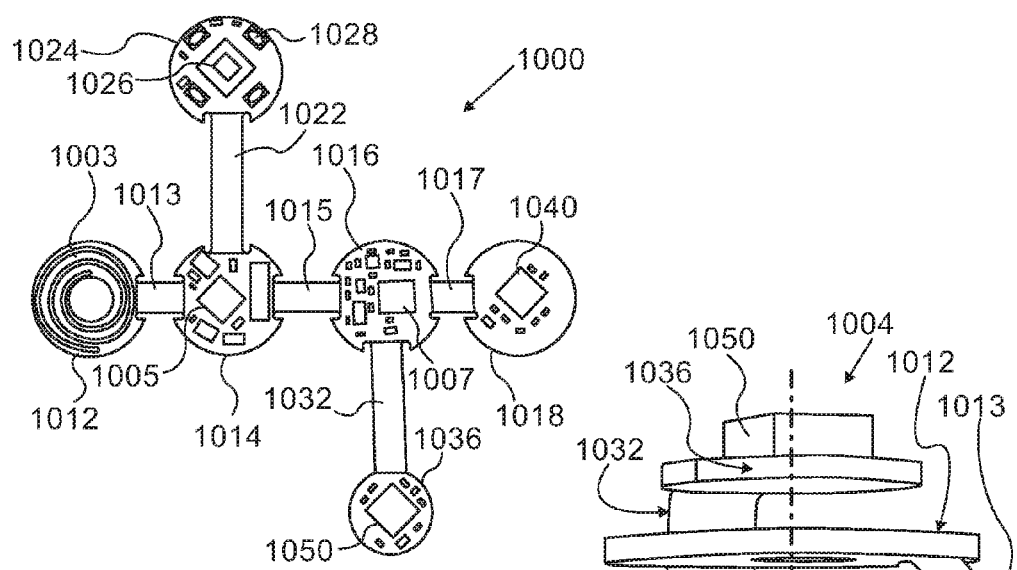
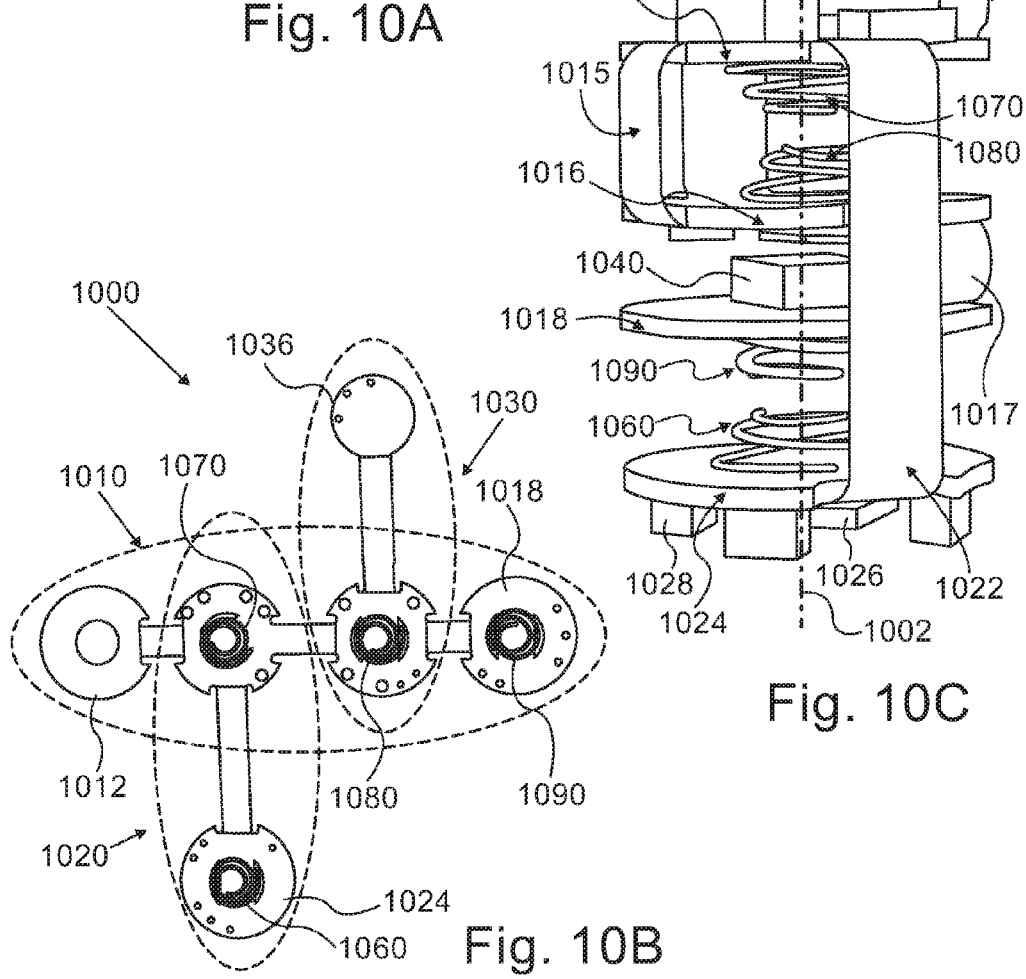
Fig. 10A
Fig. 10C
Fig. 10B

METHOD AND SYSTEM FOR DETERMINING A DEVICE MOVEMENT IRRESPECTIVE OF MOVEMENT OF A REFERENCE FRAME

CROSS-REFERENCE TO RELATED APPLICATIONS

This application is a National Phase Application of PCT International Application No. PCT/IL2014/050133, entitled "METHOD AND SYSTEM FOR DETERMINING A DEVICE MOVEMENT IRRESPECTIVE OF MOVEMENT OF A REFERENCE FRAME", International Filing Date Feb. 6, 2014, published on Aug. 14, 2014 as International Publication No. WO/2014/122655, which in turn claims priority from U.S. Provisional Application No. 61/762,401, filed Feb. 8, 2013, all of which are incorporated herein by reference in their entirety.

FIELD OF THE INVENTION

The present invention generally relates to detection of movement of objects (e.g., in-vivo sensing capsules, endoscopy capsules, etc.), and more specifically to an object capable of detecting its movement in a non-stationary three-dimensional frame irrespective of movement of the three-dimensional frame.

BACKGROUND

In-vivo measuring systems are known in the art. Some autonomous capsule like in-vivo devices, which traverse the gastrointestinal ("GI") system, may include an imaging sensor, or imager, for imaging (e.g., acquiring images of) the interior of the GI system, and a transmitter for transmitting image frames to an external system (e.g., data receiver/recorder). An in-vivo device may include sensors of other types (e.g., pH, pressure and temperature), and/or various types of tools (e.g., micro electro-mechanical system), for example to perform surgical operations in vivo and/or to administer medication in the GI system, for example from a container contained in an in-vivo device. An in-vivo device may be capable of changing a rate at which image frames are acquired).

Some in-vivo devices are configured to transmit image frames (with or without additional sensory data) to an external system (e.g., data receiver/recorder) at some constant frames per second ("FPS") rate, for example at a rate of four FPS. Other devices may be configured to transmit image frames at a rate that depends on, or is a function of, for example, movement of the in-vivo device. For example, when a device moves slowly, a relatively slow FPS rate may be preferable (e.g., to save battery energy), whereas when a device moves faster, a higher FPS rate may be preferable (e.g., to obtain or maintain a certain rate of frames per unit of intestine's length).

An in-vivo device capable of varying its FPS rate and external systems (e.g., receiver/recorder) capable of transmitting a command to the in-vivo device to change its FPS rate may be said to have an adaptive frame rate ("AFR") capability. (Typically, a decision regarding movement of an in-vivo device that has an AFR capability is taken externally, for example by an external receiver or recorder, based on, for example, image data or other information that the external system may receive from the in-vivo device.)

While AFR capability of an in-vivo device is beneficial, this capability cannot be used if the external receiver/recorder with which the in-vivo device cooperates does not have AFR capability. It would be beneficial to have an in-vivo device that can exercise AFR even if the external receiver/recorder is AFR-incompatible, and, in general, it would be beneficial to have an in-vivo device that can execute also other movement-dependent commands independently of the external receiver/recorder (e.g., autonomously).

SUMMARY OF THE INVENTION

Embodiments of a method are provided for conditional execution of a command by a swallowable in-vivo device, where the device may move relative to a non-stationary, three-dimensional, reference frame (e.g., GI system, earth) and configured to execute the command in response to a command-warranting movement. Embodiments of a system using or performing embodiments of the method are also provided.

Embodiments of the invention may include predefining a group of fiducial command-invoking movements ("CIMs") of, or for, an in-vivo sensing device, and characterizing each fiducial CIM spectrally and/or temporally. Fiducial CIMs are reference CIMs against which movements of the in-vivo sensing device are equated in order to determine whether the device's movements are (potential) CIMs. (A fiducial CIM may be characterized spectrally, or temporally, or both spectrally and temporally, independently of other fiducial CIMs, or depending on, or in conjunction with, other fiducial CIMs.) A fiducial CIM, or a CIM represented by a fiducial CIM, may be, represent, include, or otherwise be associated with a device movement that, when detected by a sensor of the device, may invoke a predetermined command associated with the detected movement. (Such a device movement is referred to herein as a "command-invoking movement", or "CIM".) A predetermined command associated with a particular CIM, or group of CIMs, may be, for example, a command to change a rate at which an imager or camera of the in-vivo device acquires, or captures, images in the GI system, or a command to change a mode of operation or state of the in-vivo device (e.g., a command to switch the device "off" when the device is in a particular location in the GI tract, or to substitute reference data, or activate or deactivate a system or sensor in the in-vivo device, etc.), or a command to transmit a message to a receiver external to the in-vivo device, etc. The predetermined command may be a command that, when executed, triggers a series of predetermined operations.

A fiducial CIM may also, or additionally, be characterized according to, or factor in, the orientation and/or location of the in-vivo device. For example, a certain movement of the in-vivo device may be classified or regarded as, or determined to be, a CIM only if the device is in a particular location in the GI system (e.g., stomach, small bowel, etc.) and/or has a particular spatial orientation. A particular device movement may be regarded as a CIM when the device movement occurs at a particular location and/or in some orientation in the GU system, or as a non CIM (e.g., as noise) when it occurs at another location or in another orientation. A fiducial CIM may be selected for use according to the location and/or orientation of the in-vivo sensing device, for example it may be used to detect a CIM, or refrained from being used, depending on the location and/or orientation of the in-vivo device, for example, in the GI system. For example, in one embodiment when the device is in the stomach, a movement signal including three movement signals corresponding to three-dimensional movement of the device movement (i.e., movement in three directions) may be analyzed to detect a CIM. When the device is, for example, in the small bowel, in one embodiment only a movement signal representing one-dimensional movement of the device may be analyzed to detect a CIM.

Embodiments of the present invention may include obtaining a movement signal (e.g., by using images captured in vivo by the in-vivo device, or by using an acceleration sensor, magnetometer, gyroscope, etc.) representative or indicating a movement of the in-vivo device, detecting movement in or from the movement signal, and determining whether the detected movement is a CIM or, for example, an interference movement. (In other words, a detected movement may be analyzed in order to classify it as a CIM or as an interference movement, depending on analysis of the detected movement.) Determining whether a detected movement is a CIM or not may be based on comparison of spectral characteristics or temporal characteristics, or both spectral and temporal characteristics, of the detected device movement to pre-stored spectral and/or temporal characteristics of fiducial CIMs and, optionally, also of interference movements. If, based on the comparison result, the detected device movement is determined to be (i.e., it is classified as) a CIM, the in-vivo device may execute the predetermined command associated with the CIM, and if the detected movement is determined not to be CIM (e.g., it is classified as an interference movement), the in-vivo device may refrain from executing any command that is invokeable by a movement (e.g., the in-vivo device may ignore such movements). A CIM (and a corresponding fiducial CIM may be characterized accordingly) may be selectable for use from a group consisting of: movement of the in-vivo device due to muscle contraction(s) of the small bowel, movement of the in-vivo device due to muscle contraction(s) of the colon, movement of the in-vivo device due to muscle contraction(s) of the stomach, and movement of the in-vivo device due to intestine constipation. (A device movement may be regarded as a CIM; e.g., after comparing it to one or more fiducial CIMs, using, or as per, other or additional criteria.)

Embodiments of the present invention may also include defining a group of interference movements that may occasionally be superimposed on, and interfere with, a CIM, or CIMs, sensed by an in-vivo device. Each interference movement, which is a movement of the device that should not invoke a command, may be characterized spectrally and/or temporally. An interference movement may be a movement selectable from a group consisting of: movement of the in-vivo device due to human's body gestures (e.g., moving a hand in any direction and with any speed, bending the subject's body forward, changing body's position, etc.), movement of the in-vivo device due to walking, respiration and heart beating. In general, any movement that is superimposed on the movement of the GI portion containing the in-vivo device, may be regarded as extraneous movement, and, therefore, as interference movement. Movements of the in-vivo device which are not due to the activity of the GI system/anatomy, and movements of the in-vivo device which are due to movement of a remote portion of the GI system (e.g., GI portion not containing the in-vivo device) are example extraneous/interference movements. (Other, or additional, types of movements may be regarded as extraneous/interference movements.)

Detecting a CIM in or from the movement signal may include filtering out or removing an interference movement from the movement signal, for example by analyzing the movement signal spectrally and/or temporally vis-a-vis pre-stored spectral characteristics and/or temporal characteristics that are known to characterize interference movements. Analyzing a movement signal 'vis-a-vis' pre-stored characteristics, as used herein, may refer to an analysis process that includes comparing spectral characteristics, or temporal characteristics, or both spectral and temporal characteristics of a detected movement or movement signal, to stored characteristics that are known to characterize spectrally, or temporally, or both spectrally and temporally predetermined interference movements or predetermined CIMs, as the case may be. Filtering out or removing interference movement(s) from the movement signal may result in an interference movement free movement signal. After interference movement(s) is/are removed (filtered out) from the movement signal, the interference movement(s) free signal may represent, embody or include a movement that may potentially be a CIM. A movement detected in the interference movement(s) free signal may be regarded as a potential CIM if the detected movement resembles a fiducial CIM spectrally. A final decision, regarding whether the potential CIM is, or is not, a CIM, may be made based on temporal analysis of the potential CIM vis-a-vis pre-stored temporal characteristics of interference movements. A decision, regarding whether a potential CIM is, or is not, a CIM, may also depend on the location of the in-vivo device in the GI system and/or on the spatial orientation of the in-vivo device. The movement signal, or an interim processing result thereof, may be analyzed spectrally and/or temporally one or more times, or iteratively or repeatedly, and at any order (e.g., first spectrally and then temporally, or vice versa) before the final decision is made. For example, removing an interference movement from the movement signal may include analyzing the movement signal spectrally and then temporally, or temporally and then spectrally, using known spectral and temporal characteristics, and/or using information indicative of a location and/or an orientation of the in-vivo device. According to another example, removing an interference movement from the movement signal may include analyzing the movement signal by iteratively or alternately performing spectral analysis and temporal analysis.

Determining whether a movement detected in a movement signal, or in an interference movement free movement signal, is a CIM may include repeatedly or iteratively applying spectral analysis and/or temporal analysis to the movement signal vis-a-vis known, or reference, spectral and/or temporal characteristics. Determining whether a detected movement is a CIM may include analyzing the related movement signal spectrally and then temporally, or temporally and then spectrally. Determining whether the detected movement is a CIM may include analyzing the movement signal by iteratively or alternately performing spectral analysis and temporal analysis. A movement signal may include three movement signals respectively corresponding to three directions or represent movement is three directions.

A movement of the in-vivo device may be classified as a CIM or as an interference movement also depending, or based, on the location and/or orientation of the in-vivo device relative to the three-dimensional reference frame. The three-dimensional reference frame may be the GI tract, or a portion thereof containing the in-vivo device, or earth.

The in-vivo device may include a movement detection unit ("MDU") that may include one or more movement sensors (e.g., acceleration sensor(s)) for detecting movement of the in-vivo device, a processor (in conjunction with a frequency analyzing unit ("FAU") and time analysis unit ("TAU") to analyze the MDU's output spectrally and/or temporally and, based on the analysis, to determine the type of movement (CIM or non-CIM; e.g., interference movement), and a controller to execute a predetermined associated command if the processor determines that the detected movement is a CIM. The in-vivo device may have a longitudinal axis and include one acceleration sensor whose sensitivity direction/axis coincides with the longitudinal axis of the in-vivo device, or is at an angle relative to the longitudinal axis. The in-vivo device may also include a foldable printed circuit board ("PCB") on which the MDU, FAU, TAU, processor and/or controller, etc. (e.g., camera, other sensors) are mounted.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIGS. 3A-3B show example spectral content of typical movements according to embodiments of the present invention;

FIG. 4 shows a movement detection unit ("MDU") according to an embodiment of the present invention;

FIG. 5 shows a frequency analyzing unit ("FAU") according to an embodiment of the present invention;

FIG. 6A shows a time analyzing unit ("TAU") according to an embodiment of the present invention;

FIGS. 6B-6C demonstrate typical movement decisions according to embodiments of the present invention;

FIG. 7 shows a TAU according to an embodiment of the present invention;

FIGS. 10A-10C depict a printed circuit board according to an example embodiment of the present invention.

DETAILED DESCRIPTION OF THE INVENTION

The description that follows provides various details of exemplary embodiments. However, this description is not intended to limit the scope of the claims but instead to explain various principles of the invention and the manner of practicing it.

Due to the nature of GI peristalsis, an accelerometer is a 'natural' candidate for sensing movement of an autonomous in-vivo device (e.g., in-vivo imaging capsule) in the gastrointestinal system. That is, an accelerometer is a natural candidate for sensing movement of an autonomous in-vivo device because a movement of an in-vivo device is to be detected relative to the GI tract, which has a dynamically changing posture. Therefore, the GI tract can be regarded as a non-stationary, three-dimensional, reference frame. That is, the GI tract reference frame is 'non-stationary' for two reasons: (1) the GI tract can change its posture (e.g., as a result of intestine activity or body movement), and (2) the reference frame may be 'local', meaning that the reference frame's coordinates spatial directions are determined as per a GI portion currently containing the in-vivo device. (The reference frame may be regarded as moving along with the in-vivo device.)

In addition, since acceleration of a body or body parts (e.g., arms, legs, etc.) is far lower than (hence ignorable comparing to) acceleration of the in-vivo device in the GI tract, using an accelerometer inherently provides for some filtering of accelerations due to such extraneous movements. Accelerometers typically use a weight or strain gauge that can move, or is sensitive, only in a certain direction in response to acceleration force, so that the accelerometer can sense accelerations only in that particular direction that is referred to herein as 'sensitivity direction' or 'sensing direction'.

Figures 1A, 1B, 1C:
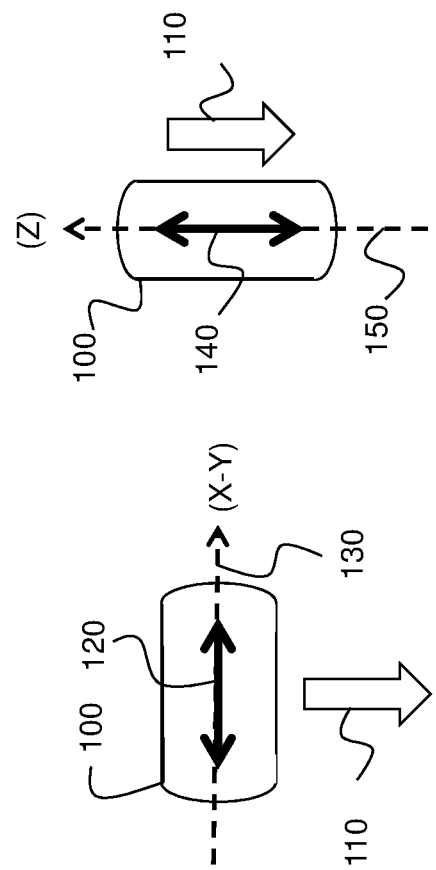
FIGS. 1A-1C show a capsule type in-vivo device in three, typical, positions relative to gravity force according to embodiments of the present invention.

FIGS. 1A through 1C show a capsule type in-vivo sensing device 100 in three typical positions relative to the direction of earth's gravity according to an embodiment of the present invention. FIG. 1A shows movements of in-vivo device 100 in direction 120, in plane X-Y 130, that is perpendicular to the direction 110 of gravity. An acceleration sensor sensitive to acceleration in a direction coinciding with, or lying on, the X-Y plane 130 is insensitive to gravity because, in FIG. 1A, the weight used to sense/measure acceleration can move horizontally (in direction 120) but not in other directions; e.g., in direction 110 which is the gravitation direction. A movement signal that would be output from an acceleration sensor whose sensitivity/sensing direction is perpendicular to the direction of gravity force would be insensitive to walking steps' impact because walking steps typically elicit/produce acceleration/deceleration force in a direction that substantially coincides with the gravity's direction 110, which is orthogonal to the sensor's sensitivity/sensing direction 130. (A different situation is shown in FIG. 1B, where the sensor's sensitivity/sensing direction 150 substantially coincides with gravity's direction 110.)

It may be determined that movement of capsule 100 in direction 120 may be regarded as a movement worth analyzing (e.g., to determine if it is a command-invoking movement or an interference movement) if the acceleration signal, which the accelerometer outputs, has a value V(acc) that is greater than some predetermined positive threshold value Vth, or smaller than a negative value −Vth; that is, if condition (1) is met:

$$V(acc) > +Vth \text{ (or } V(acc) < -Vth)  \quad (1)$$

FIG. 1B shows movements of in-vivo device 100 in direction 140, in the Z axis/direction 150 that coincides with the direction 110 of gravity. An acceleration sensor sensitive to acceleration in a direction coinciding with the Z direction 150 is sensitive to gravity because, in FIG. 1B, the weight used to sense/measure acceleration can move vertically, in direction 140 that is the gravitation's direction. Sensitivity of an accelerometer to gravity means that the accelerometer's weight deviates from, or is biased or decentered from the weight's balanced, or neutral, position due to the gravitational force. Such deviations may (if not compensated for) erroneously indicate that the device including the accelerometer is accelerating. The accelerometer's erroneous position due to gravity must, therefore, be compensated for.

As in FIG. 1A, it may be determined that movement of device 100 in direction 140 may be regarded as a movement worth analyzing (e.g., to determine if it is a command-invoking movement or interference movement) if the acceleration signal, which the accelerometer outputs, has a value that is greater than some predetermined threshold value biased by (in this case by the full effect) of gravity (g); that is, if condition (2) is met:

$$V(\text{acc}) > g + Vth \text{ (or } V(\text{acc}) < g - Vth) \qquad (2)$$

FIG. 1B shows a situation where the sensor's sensitivity/sensing direction 150 substantially coincides with the gravity's direction 110. Under these circumstances, a movement signal that would be output from the acceleration sensor would be most sensitive to the impact of walking steps.

FIG. 1C shows movements 160 of in-vivo device 100 in direction 170, which is at angle of 45 degrees (the angle is shown at 180) relative to the gravity direction 110. Since the gravity vector has a component in direction 170, which is the accelerometer's sensitivity/sensing direction, the accelerometer is sensitive to gravity, though less than when the accelerometer's sensitivity/sensing direction coincides with the gravity's direction (as demonstrated by FIG. 1B). All accelerometer sensitivity/sensing directions that are not perpendicular to the gravity's direction result in erroneous indications due to some gravity effect, that the device including the accelerometer is accelerating (moving). (The more an accelerometer sensitivity/sensing direction is parallel to the gravity direction, the greater the effect gravity has on the accelerometer's output signal and, therefore, the greater the acceleration measurement error.) The accelerometer's erroneous position due to gravity must, therefore, be compensated for.

As in FIG. 1A and FIG. 1B, it may be determined that movement of capsule in direction 170 may be regarded as a movement worth analyzing (e.g., to determine there from if it is a CIM or interference movement) if the acceleration signal, which the accelerometer outputs, has a value that is greater than some predetermined threshold value which is biased due to some effect (E) of gravity (g) that depends on the angle α (shown at 180, FIG. 1C) between the acceleration sensitivity/sensing direction 170 and the gravity's direction 110; that is, if condition (3) is met:

$$V(\text{acc}) > g^* \cos(\alpha) + Vth \text{ (or } V(\text{acc}) < g^* \cos(\alpha) - Vth) \qquad (3)$$

Since the threshold value against which V(accelerometer) is compared depends on angle α (180, FIG. 1C), and α cannot be determined if the an in-vivo device's orientation cannot be determined, condition (3) above may result in erroneous decisions regarding movements of the in-vivo device. In order to obtain a reliable measurement of the movement of the in-vivo device regardless of the angle alpha (180), the effect of gravity has to be neutralized, or compensated for, completely regardless of the value of angle α. FIG. 1C shows a situation where the sensor's sensitivity/sensing direction 170 is at angle with respect to the gravity's direction 110. Under these circumstances, a movement signal that would be output from the acceleration sensor would be sensitive to the impact of walking steps to some extent.

Figure 2:
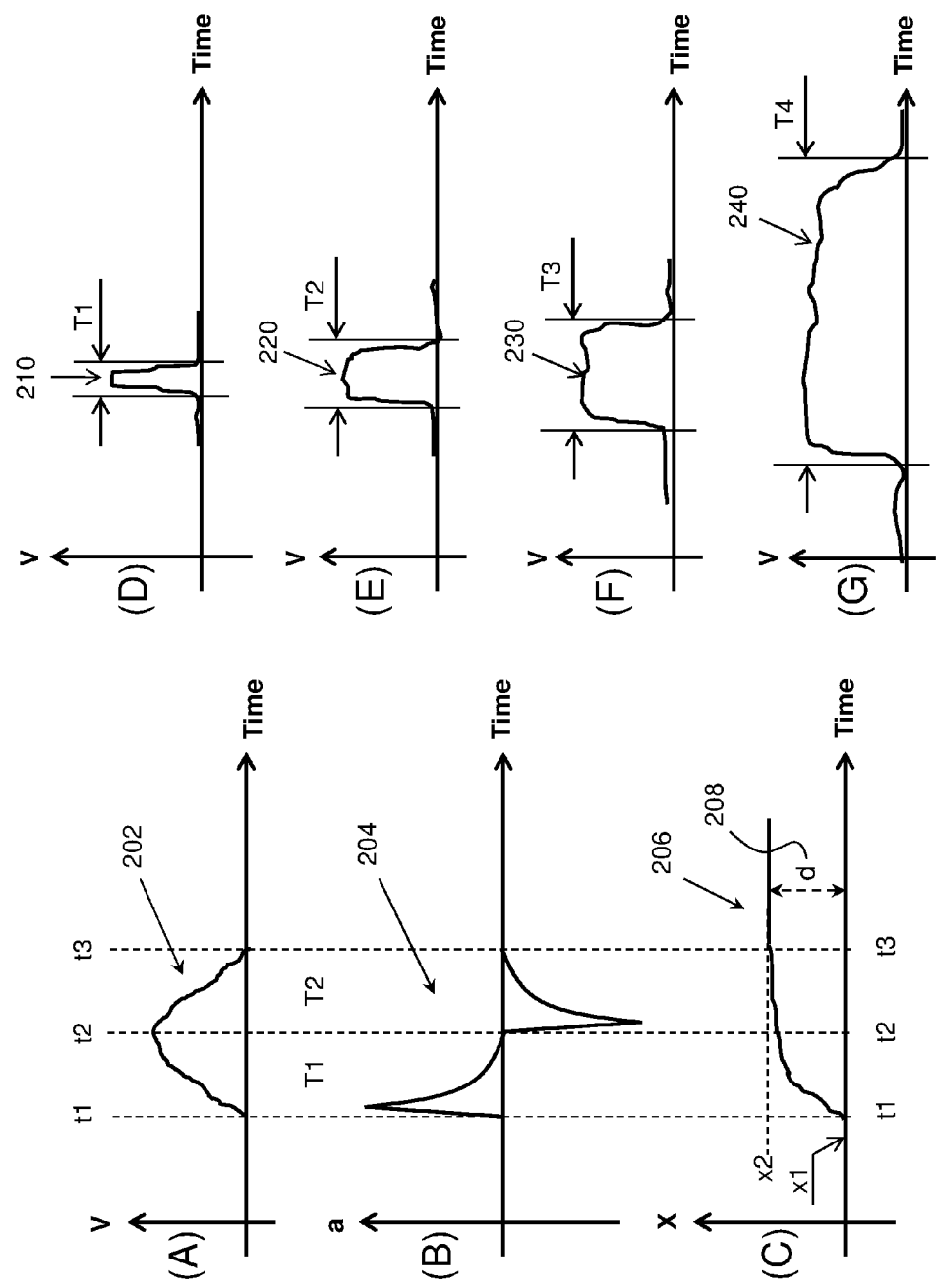
FIGS. 2A-2C respectively show velocity, acceleration and distance curves associated with movement of an autonomous in-vivo device according to embodiments of the present invention.
FIGS. 2D-2G show typical movements associated with movement of an autonomous in-vivo device according to embodiments of the present invention.

FIGS. 2A-2C respectively show velocity (202), acceleration (204) and distance (206) curves associated with movement of an autonomous in-vivo device according to embodiments of the present invention. A swallowable autonomous in-vivo sensor (e.g., in-vivo imaging device) typically moves in the GI tract in a pulsating pattern that is governed by peristalsis. A typical movement event/occurrence, of such a device is shown at 202 in FIG. 2A. The movement event starts at time t1, when the velocity V(t) is zero, and the velocity increases until it reaches its peak at time t2, and then decreases until it becomes zero at time t3. Curve 204 of FIG. 2B shows the acceleration/deceleration corresponding to velocity curve (movement event) 202, and curve 206 of FIG. 2C shows the distance, d (shown at 208 in FIG. 2C), traveled by the in-vivo device during velocity pulse/event 202 (during time period t1-t3), where d is equal to the difference between point x1 (the initial position of the device at time t1) and point x2 (the position of the device at time t3).

FIGS. 2D-2G show examples of four movement events (210, 220, 230 and 240) according to embodiments of the present invention. (The vertical axis in FIGS. 2D-2G denotes velocity, V.) FIG. 2D shows a relatively fast, spike-like, movement event 210 of a relatively short duration T1; FIG. 2E shows a relatively slower movement event 220 of duration T2 (T2>T1); FIG. 2F shows a slower movement event 230 of duration T3 (T3>T2>T1), and FIG. 2G shows the slowest movement event 240 of duration T4 (T4>T3>T2>T1). Some device movements may pertain to (caused by) extraneous (noise) movements in the sense described herein, and other device movements may pertain to, or be, CIMs. For example, movement event 210 may be sensed due to (caused by) an impact of a walking step or due to coughing; movement event 220 may typically be, represent or pertain to movement of an in-vivo device in the colon; movement event 230 may typically be, represent or pertain to a movement event of the in-vivo device in the small bowel, and movement 240 may typically be, represent or pertain to a body gesture (e.g., moving a hand or leg, bending over or sideways, etc.). Body gestures, which are regarded as noise/interference movements (and therefore they should not invoke a command or cause a command to be invoked) are usually slow relative to movements of an autonomous in-vivo device due to peristalsis.

Each device movement represented by a movement event shown in FIGS. 2E-2G, and possibly other types of movements, may be characterized spectrally to distinguish between them. However, in some cases, analyzing device movements only spectrally may not suffice to determine if a certain device movement is, represents or derived from, a CIM or not. That is, a detected movement event may resemble a CIM spectrally. However, a following temporal analysis of the movement event may result in a conclusion that it is not a CIM. That is, temporal analysis of a movement event that is spectrally assumed to be, or suspected as representing, a CIM helps 'putting' the suspected movement in a right 'context', as demonstrated below, for example in connection with FIGS. 6B-6C. (A particular movement that, after spectrum analysis, is initially assumed to be a CIM may be analyzed temporally in conjunction with adjacent movement events in order to corroborate the assumption or to refute it.)

FIGS. 3A-3B show spectral content of typical device movements according to example embodiments of the present invention. FIG. 3A shows a spectrum 310 of a device movement that, based only on frequency analysis, may resemble a CIM. Also shown in FIG. 3A is a direct current ("DC") component 320 due to the gravity (g) force, and a high pass filter ("HPF") 330 that filters out or removes the DC component 320. As explained above, other types of movements (e.g., movements having similar frequency components as a CIM, or higher frequency components) may be sensed, which are not to invoke a command invokeable by a CIM's type of movement. (Such movements are regarded as noises or interference movements that have to be ignored or filtered out or removed too).

FIG. 3B shows spectrums 310, 320 as in FIG. 3A, and, in addition, a spectrum 340, which may characterize or represent relatively slow movements that should not invoke a command (but they may erroneously invoke a command if they are not cancelled out or removed), and a spectrum 350 that may characterize or represent relatively fast movements that also should not invoke a command (but they may invoke it if they are not cancelled out or removed). While HPF 330 of FIG. 3A may filter out or remove the DC component (320), and, if designed properly, all, or most of, the slow movements (340), it may pass high frequency components representing or making up fast movements (e.g., movements 350) that also should not invoke a command (but they may do so if they are not cancelled out). Therefore, a band pass filter ("BPF") 360 may be used to pass only frequency spectrum representing, corresponding to or making up movements that can initially/potentially be regarded as a CIM. A device movement may initially be regarded as, or determined to be, a potential CIM after analyzing it vis-a-vis fiducial CIMs. Analyzing a movement (event) vis-a-vis a fiducial CIM may include comparing frequency spectrum of the movement (event) to frequency spectrum of the fiducial CIM, and/or calculating temporal correlation between the movement (event) and the fiducial CIM.

FIG. 3B shows one BPF (360) by way of example. However, the number of BPFs that may be used may vary according to the number and frequency characteristics of the movements that have been predefined as command invoking movements, and/or of movements that are worth further checking (e.g., by temporally analyzing them individually or collectively) whether they, indeed, are (or one of them is) a CIM. A filter used to detect resemblance between movement events and CIMs may be a matched filters array module ("MFAM").

FIG. 4 shows a movement detection unit (MDU) 400 according to an embodiment of the present invention. MDU 400 may include an acceleration sensor(s) unit ("ASU") 410 that may include one acceleration sensor or more than one acceleration sensor (e.g., two acceleration sensors, three acceleration sensors, etc.) for sensing acceleration in one or more directions/axes. MDU may, in general, include one or more sensors selected from a group consisting of accelerometer (to sense acceleration), magnetometer (to sense location and orientation) and gyroscope (to sense orientation). MDU 400 may also include a transducer 420 for converting the acceleration(s) sensed by the acceleration sensor(s) into a corresponding analog movement signal(s), an anti-aliasing circuit 430 to remove sampling side effects, an analog-to-digital converter ("ADC") 440 for converting the (analog) movement signal(s) into digital data, and a processing and analyzing unit ("PAU") 450. PAU 450 may include a memory unit 492. Memory unit 492 may store, among other things, the digital data representing the analog movement signal(s), and information/data representing fiducial CIMs (e.g., frequency and/or temporal characteristics of fiducial CIMs) and interference movements (e.g., frequency and/or temporal characteristics of interference movements). Memory unit 492 may also store time specifics defining time templates against which movement events may be compared or analyzed in order to corroborate or refute an initial determination, or assumption, that a device movement, which frequency-wise resembles a fiducial CIM (e.g., a PCIM), is a CIM.

PAU 450 may also include a frequency analyzing unit (FAU) 460 to analyze movement signals/events spectrally (e.g., by comparing frequency characteristics of them to frequency characteristics of stored fiducial CIMs), a time analyzing unit (TAU) 470 to analyze movement signals/ events temporally (e.g., by comparing time characteristics of them to time characteristics of stored fiducial CIMs and/or to stored time specifics of time templates), a comparator 480 to compare spectral features of the spectrally analyzed movement signals/events to frequency characteristics stored in the memory, and to compare temporal features of the temporally analyzed movement signals/events to temporal characteristics stored in the memory. FAU 460 may include or use a frequency filter (e.g., BPF) or a set of frequency filters (e.g., multiple BPFs), or matched filters (array) to detect frequency features of the analyzed movement signal(s)/events. TAU 470 may include or use one or more timers and/or counters to detect time features of the analyzed movement signal(s)/events. Comparator 480 may include or use a correlator to determine the extent to which the frequency and time features of the analyzed movement signal(s)/events respectively resemble one or more of the spectral and temporal characteristics which are pre-stored in memory 492.

PAU 450 may also include a controller 490 to control, among other things, operation of FAU 460 (e.g., set its filters' boundaries/windows/coefficients, etc.), TAU 470 (e.g., set and reset a timer or a counter, etc.) and comparator 480 (e.g., determine which frequency and time feature should respectively be compared to which pre-stored spectral characteristics and temporal characteristics), and, ultimately, to determine if a movement event sensed by movement sensor 415 is, or includes, a CIM. If controller 490 determines that a movement event sensed by movement sensor 415 is, or includes, a CIM, controller 490 may execute the command associated with the movement event, or cause (e.g., instruct) another device to execute the command. In one embodiment, if controller 490 determines that a movement event sensed by movement sensor 415 is, or includes, a CIM, controller 490 may execute the same command (or instruct another device to execute the command) regardless of the type of the command-invoking movement. (The same command may be invoked by all movements that are determined by controller 490 to be CIMs.) In another embodiment, a command may be executed as per one CIM or as per a group of CIMs. (A particular command may be invoked only by (e.g., assigned to) a specific CIM, e.g. on a command-per-movement's type basis, or by (e.g., assigned to) a specific group of CIMs.) Controller (or processor) 490 (or controller or processor 818 of FIG. 8), by executing software or instructions, may carry out steps/procedures which are performed by any one or more of FAU 460, TAU 470, FAU 500, TAU 600 and TAU 700, and thus may function as these units. Each of controller or processor 490, 818 may be or include computer processors, central processing units, etc.

An in-vivo device identical or similar to the one shown in FIG. 8 (in-vivo device 810, described below), may include a MDU (e.g., MDU 828) that may function like, or in a similar way as, MDU 400, for example.

PAU 450 may also include a magnetometer or a gyroscope to facilitate determination of the spatial orientation of in-vivo device relative to, for example, earth, or to another reference frame or coordinate system.

FIG. 5 shows a frequency analyzing unit (FAU) 500 according to an example embodiment of the present invention. FAU 500 may include or use a matched filters array module (MFAM) 510. MFAM 510 may receive movement data (512), or movement signal, that may be output or transferred, for example, by/from an ADC (e.g., ADC 440), and use various BPFs to cancel/filter out, or remove, noise signals due to, for example, interference movements and other noises. MFAM 510 may output signals that are spectrally resembling, or representing, CIMs. MFAM 510 may include as many BPFs as there are CIMs. For example, MFAM 510 may include one BPF for each type of CIM. MFAM 510 may detect frequency features in movement data/signal 512, and output (514) data or signal that represents detected movement events, where each detected movement event may potentially be a CIM.

FAU 500 may also include or use a potential CIM detector ("PCIMD") 520 to analyze the detected movement events spectrally (e.g., vis-a-vis fiducial CIMs) in order to detect movement events that resemble CIMs. PCIMD 520 may detect a movement event that resembles a CIM by analyzing the frequency features output (514) by, or transferred from, MFAM 510 vis-a-vis frequency features of fiducial CIMs. (A movement event resembling a CIM is regarded herein as a 'potential CIM' that is subjected to a CIM corroboration/refutation process.)

PCIMD 520 may output (522), for example in real-time, a (continuous) series of 'decision' pulses where each decision pulse may denote or represent a detected movement event that is a potential CIM. An example series of pulses corresponding to or representing a series of such movement events is shown at 524. By way of example, pulse/decision series 524 is shown having two distinct levels (530 and 540) and three detected movement events 551, 552 and 553 that are regarded as potential CIMs. Level 530 may indicate, or be associated with, a detected movement, and level 540 may indicate, or be associated with, absence of movement. (The functionalities of the two levels may be swapped, and the number of detected movement events, and their temporal spacing and width, may vary according to the number, frequency and type of the detected movements.) By way of example, movement event 551—the first detected potential CIM—starts at time t1 and has time duration T1; movement event 552—the second detected potential CIM—starts at time t2 and has time duration T3 that may differ from T1, and movement event 553 starts at time t3 and has time duration T5 that may differ from T1 and T3. (Time periods T2 and T4, which may be different, are periods determined by PCIMD 520 as not including movement event(s) that resemble CIMs.)

Time specifics (e.g., relative occurrences, start times, time durations, etc.) of all the movement events may be stored in a memory similar to the memory mentioned in connection with PAU 450 (FIG. 4) for time analysis. Times t1, t2, t3, and time periods T1, T2, T3, T4 and T5 are example of time specifics that may temporarily be stored and analyzed to enhance the determination process regarding whether a potential CIM (a non-interference movement) is, indeed, a genuine CIM. Time analysis is used to rule out an interference movement, or other noise signal, that resembles a CIM spectrally. That is, while spectral analysis of a particular movement may result in the assumption that a particular movement is a CIM (e.g., that the particular movement is a PCIM), temporal analysis of a series of movements including the particular movement may either corroborate the assumption or refute it. In other words, the particular PCIM may be analyzed vis-a-vis one or more interference movements in order to determine whether the particular PCIM is a CIM or an interference movement.

Enhancing the aforesaid determination process may include determining the location of a movement event/pulse (e.g., movement event/pulse 551) relative to other movement events/pulses (e.g., to adjacent movement events/pulses) in the series, or to the density of the movement pulses. Other time criteria may be used to enhance the aforesaid determination process. For example, a pattern of movement pulses (e.g. movement pulses 551, 552 and 553) may be compared to one or more pre-stored time templates, or time specifics, that may characterize one or more interference movements, and if a particular movement pulse (e.g., movement pulse 552), along with e.g., its adjacent movement pulses, does not match any of the time templates, it may be decided that particular movement pulse is a CIM. Otherwise (the particular movement pulse, along with e.g., its adjacent movement pulses, does match a time template), it may be decided that the particular movement pulse is not a CIM (e.g., it is an interference movement). For example, applying spectral analysis on a movement signal may provide frequency features that may resemble frequency features of a CIM (e.g., movement due to a colon contraction), and, consequently, may result in a movement pulse, e.g. movement pulse 551. However, the same, or similar, frequency features may also characterize movement due to, for example, a walking step. Since each walking step may produce a similar movement pulse (e.g., movement pulses 552 and 553 are similar), and a walking pace (and hence the frequency of the movement pulses caused by walking) is known (within a known margin), a movement event/pulse may be ruled out if it is part of, or contained in, a series of movement events/pulses that collectively represent a non CIM. Similar considerations may be taken into account with respect to other types of reoccurring movement events, for example movement events recurring due to running, heartbeats, respiration process, finger tapping on a tough object, waving of a hand, etc. A movement event resulting from a CIM may also reoccur, but in this case, and in similar cases, the movement event should still be regarded as a CIM. For example, a movement event caused by, or sensed due to, a contraction of, say, the colon, may still be regarded as a CIM despite of it being part of a series of like movement events caused by peristalsis. A time analysis of a movement event, for example vis-a-vis a series of adjacent movement events, may render the determination process more reliable. (Time analysis is further described, for example, below in connection with FIGS. 6A-6C.)

FIG. 6A shows a time analyzing unit (TAU) 600 according to an example embodiment of the present invention. TAU 600 may include a memory device 610, a time pattern detector ("TPD") 620 and a movement decision logic ("MDL") 630. TAU 600 may receive (612) a series of movement pulses/events (e.g., movement pulses/events 524) that may be output/transferred by/from a FAU (e.g., FAU 500), and it may store the series of movement pulses/events in memory device 610 in order to enable analysis thereof by TPD 620. TPD 620 may compare the series of movement pulses/events (e.g., a movement pulse/pulse at a time) to one or more time templates or time specifics that may be pre-stored in memory device 610. The one or more time templates, or selected time specifics, may be derived from, correspond to or represent a series of repeating movements that, when considered as a whole, a movement pulse/event, which is part of the series of movement pulses/events, may be determined not to be a CIM (but; e.g., an interference movement). Memory device 610 may store digital data representing an analog movement signal, and information/data representing fiducial CIMs (e.g., frequency and/or temporal characteristics of fiducial CIMs) and interference movements (e.g., frequency and/or temporal characteristics of interference movements). Memory device 610 may also store time specifics defining time templates against which movement events may be compared or analyzed in order to corroborate or refute an initial determination, or assumption, that a device movement, which frequency-wise resembles a fiducial CIM (e.g., a PCIM), is a CIM.

MDL 630 may determine whether a particular movement pulse in the series of movement pulses represents a CIM based on the comparison results, and output (632) a signal indicating that a decision that the particular movement pulse is a CIM, as shown at 640, or a signal indicating that it is not a CIM, as shown at 650.

FIGS. 6B-6C show example movement pulses according to an embodiment of the present invention. FIG. 6B shows one movement pulse 660 that may be the result of, for example, a walking step that a controller (e.g., controller 490) detected. If movement pulse 660 is considered individually, it may erroneously be regarded as a movement pulse representing a CIM. FIG. 6C, on the other hand, shows a pulse series 670 of movement pulses 672, 674, 676 and 678 that may be the result of four detected walking steps. If any of movement pulses 672, 674, 676 and 678 is considered individually, it may also be decided as representing, or resulting from, a CIM. However, if any particular movement pulse of movement pulses 672, 674, 676 and 678 (e.g., movement pulse 674) is considered with respect to other (e.g., adjacent) movement pulses (e.g., adjacent movement pulses 672 and 676), thus considering it in a broader context (rather than individually), the particular movement pulse may correctly be determined by the detector to be a non CIM.

FIG. 7 shows a time analyzing unit (TAU) 700 according to an example embodiment of the present invention. TAU 700 may include an N-Pulses Register ("NPR"), or N-data cells unit ("DCUs") 710, a time pattern detector (TPD) 720, a movement decision logic (MDL) 730 and a timing unit 740. NPR (also referred to as 'DCU') 710 may receive a series of movement pulses 712 (e.g., from a FAU's output; e.g., from FAU 500), and may be configured to hold/store up to n data units at a time, in n cells (the register's cells are designated as M1, M2, M3, . . . , Mn). "Data unit" may be data including time specifics (e.g., start time, duration) representing a movement event and/or time specifics representing a non-movement period. ("Non-movement period" is a time period that precedes or succeeds a movement event.)

A data unit representing a first movement event in a series of movement events may be stored in cell M1. When a second movement event is output (or shortly thereafter), for example by FAU 500, the time specifics pertaining to a first non-movement period that follows the first movement event may be determined in order to produce a data unit representative of the non-movement period. Upon producing the time specifics representative of the first non-movement period, or shortly thereafter, the content of cell M1 may right-shift one cell; e.g., to the next cell (to cell M2), and the data unit representing the first non-movement period may be stored in cell M1. The same process may be repeated for each new movement event that the FAU outputs, such that with each new data unit that is produced, the content of each cell Mi (1≤i≤n) is right-shifted one cell, the new data unit is stored in cell M1, and the data unit stored in cell Mn is replaced by the data unit currently stored in cell Mn-1.

After a new data unit is stored in cell M1 (regardless of whether the data unit represents a movement event or a non-movement period), and the other data units are right-shifted one cell, all of the data units stored in the N data cells of DCUs 710 may respectively be transferred to n inputs (designated as a1, a2, a3, . . . , an) of time pattern detector (TPD) 720 for evaluation. TPD 720 may function in a similar way as TPD 620, and movement decision logic (MDL) 730 may function in a similar way as MDL 630. For example, MDL 730 may output (732) a first data or signal indicating a decision that a particular detected movement is a CIM, or a second data or signal indicating a decision that the particular movement is not a CIM. Timing unit 740 may time, or coordinate, data shifts in NPR (DCU) 710 and, in general, it may coordinate operations of NPR/DCU 710 and TPD 720.

Figure 8:
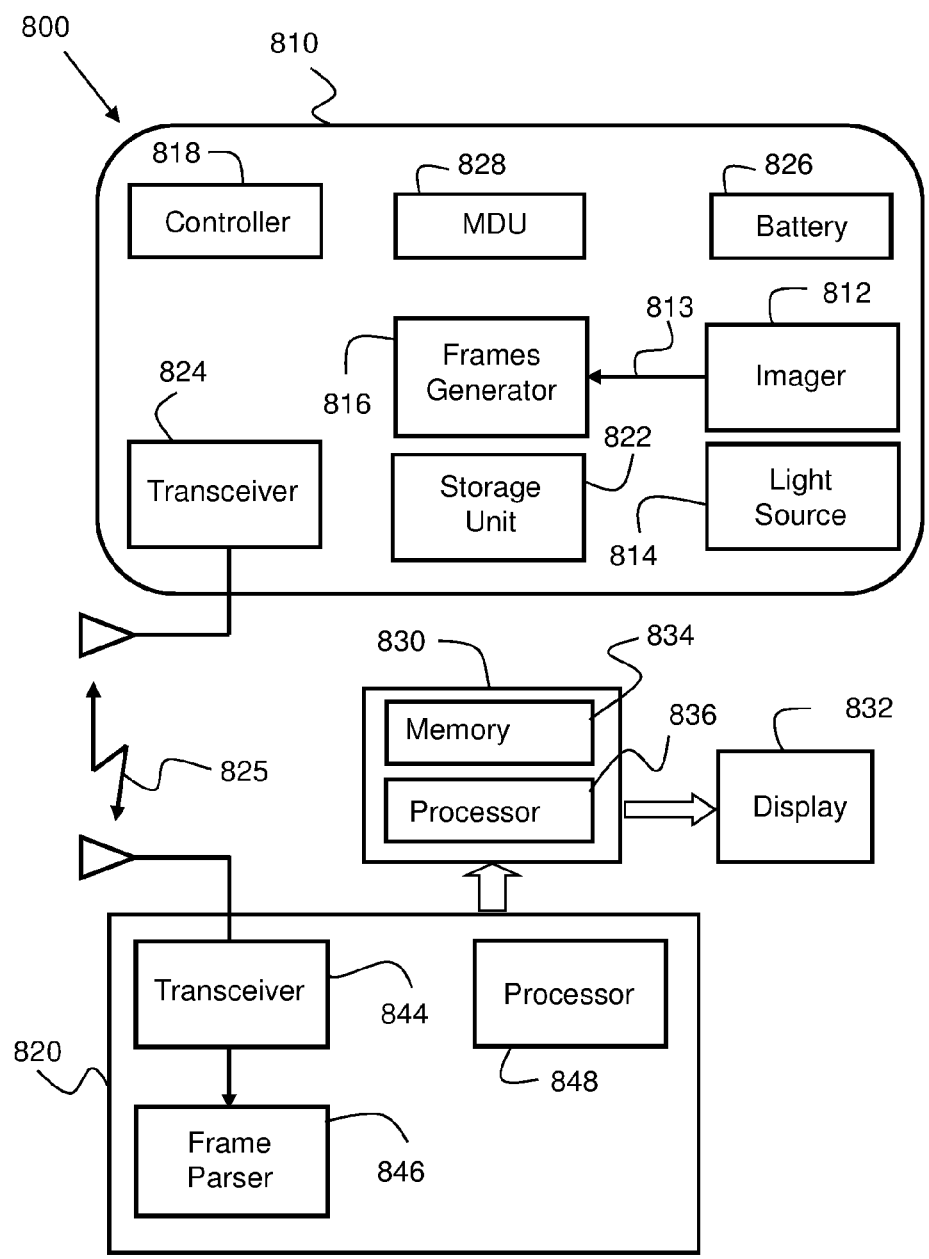
FIG. 8 is a block diagram of an example in-vivo system according to an example embodiment of the present invention.

FIG. 8 is a schematic diagram of an in-vivo imaging/sensing system 800 according to an example embodiment of the invention. In-vivo imaging system 800 may include an in-vivo imaging device 810, external (extra-body) receiver 820 that may function as a data recorder, workstation 830 (e.g., personal computer), and a display device 832. In-vivo imaging device 810 may be, for example a swallowable device, capturing images and transmitting corresponding image frames to an external receiving apparatus (e.g., to receiver 820). The image frames may be presented in real-time or after processing, be combined into an image stream for display to a user, for example by using display 832.

An in-vivo imaging device may have at least one imager and/or sensor(s) of other type(s). By way of example, imaging device 810 includes one imager; e.g., imager 812 (more than one or two imagers may be used). In-vivo imaging device 810 may also include a light/illumination source 814, a data (e.g., image data or) frame generator 816, a controller 818, a storage unit 822, a transceiver 824, and a power source 826 for powering them. Controller 818, among other things, may controllably operate illumination source 814 to illuminate areas traversed by in-vivo device 810, and coordinates the images capturing timing of imager 812. Controller 818 may momentarily store captured images and related image frames in storage unit 822. Controller 818 may also perform various calculations and store calculation results in storage unit 522.

Frames generator 816 may receive image data 813 from imager 812 and use the image data to produce an image frame ("frame" for short) for the pertinent captured image. A frame typically includes a header field that contains information and/or metadata related to the frame itself (e.g., information identifying the frame, the serial number of the frame, the time the frame, the bit-wise length of the frame, etc.). A frame may also include an uncompressed version of the image data and/or a compressed version thereof. The header may include additional sensory information. Controller 818 may operate illumination source 814 to illuminate, for example, four times per second to enable capturing four images per second, and transceiver 824 to concurrently transmit corresponding frames at the same rate or at a different rate. Controller 818 may operate illumination source 814 to capture more images per second, for example seventeen images or more than seventeen images per second, and transceiver 824 to concurrently transmit corresponding frames at the same rate. After frames generator 816 produces a frame for a currently captured image, controller 518 wirelessly communicates 825 the frame to receiver/data recorder 820 by using transceiver 824. Receiver 820 may be a stand-alone receiver that is located close enough to the person swallowing the in-vivo device in order to facilitate receiving and processing of the transmitted frames by data recorder 820.

Data recorder (receiver) 820 may include a transceiver 844, a frame parser 846, and a processor 848 for managing transceiver 844 and frame parser 846. Data recorder 820 may include additional components (e.g., USB interface, Secure Digital ("SD") card driver/interface, controllers, etc.), elements or units, for example, for communicating with (e.g., transferring frames, data, etc. to) an external processing/displaying system that may be configured to process images captured by in-vivo device 810.

Transceiver 844 may receive a frame corresponding to a particular captured image, and frame parser 846 may parse the frame to extract the various data entities contained therein (e.g., image data and, optionally, other type of sensory data).

In-vivo imaging system 800 may also include a workstation 830. Workstation 830 may include a display or be functionally connected to one or more external displays, for example to display or monitor 832. Workstation 830 may receive image frames, and other types of data from data recorder 820, and present them in real-time, for example as live video, or produce a video stream. Workstation 830 may include a memory, such as memory 834, for storing the frames (and possibly data of other types) transferred from data recorder 820, and a processor, such as processor 836, for processing the stored data (e.g., image data). Signals that are transmitted from in-vivo device 810 (e.g., by transceiver 824) may be received by antennas that are attached or laid in proximity to the body of the person swallowing the in-vivo device. The signals received by the antennas may be forwarded to data recorder 820, for analysis and interpretation, via a communication cable. (The antennas and the communication cable are not shown in FIG. 8.)

In-vivo imaging device 810 may also include a MDU 828 for detecting various types of command-invoking movements while filtering out or removing non command-invoking movements. MDU 828 may be implemented using any of the configurations described in connection with FIGS. 4, 5, 6A-6C and 7, and using any method that is described herein. For example, MDU 828 may include the components of MDU 400 (or similar components) and it may function like, or in a similar way as MDU 400. Controller 818 may be configured to function also as controller 490 of FIG. 4, or vice versa.

Functionality of a movement detection unit and the consequent execution of a predetermined command may be distributed between in-vivo device 810 and receiver/recorder 820, or among in-vivo device 810, receiver/recorder 820 and workstation 830. For example, in-vivo device 810 may detect movement of in-vivo device 810 using on-board movement sensor(s), and transmit (825) movement data to receiver/recorder 820. Receiver/recorder 820 may analyze the movement data using a FAU and/or a TAU, and, based on the analysis result, determine whether the movement detected by in-vivo device 810 is a CIM or not. If receiver/recorder 820 determines that the movement is a CIM, receiver/recorder 820 may transmit (825) to in-vivo device 810 an instruction to execute a predetermined command, for example, to change an image capturing rate, to change a mode of operation, etc.

Controller or processor 818 (or controller or processor 836, 848), by executing software or instructions, may carry out steps and/or procedures which are performed by any one or more of MDU 828, MDU 400, FAU 460, TAU 470, FAU 500, TAU 600 and TAU 700, and thus may function as these units. Each of controller or processor 818, 836, 848 may be or include computer processors, central processing units, etc. In-vivo device 810 may have a longitudinal axis, and movement sensor (which may be part of MDU 828) may include one accelerometer whose sensing direction coincides with the longitudinal axis of the in-vivo device. Components of in-vivo imaging/sensing system 800 may be similar to components used in a capsule endoscopy system commercially available from the common assignee of the present application, which capsule endoscopy system is commercially known as the PillCam® capsule, or may be similar to other capsule endoscopy systems.

Figure 9:
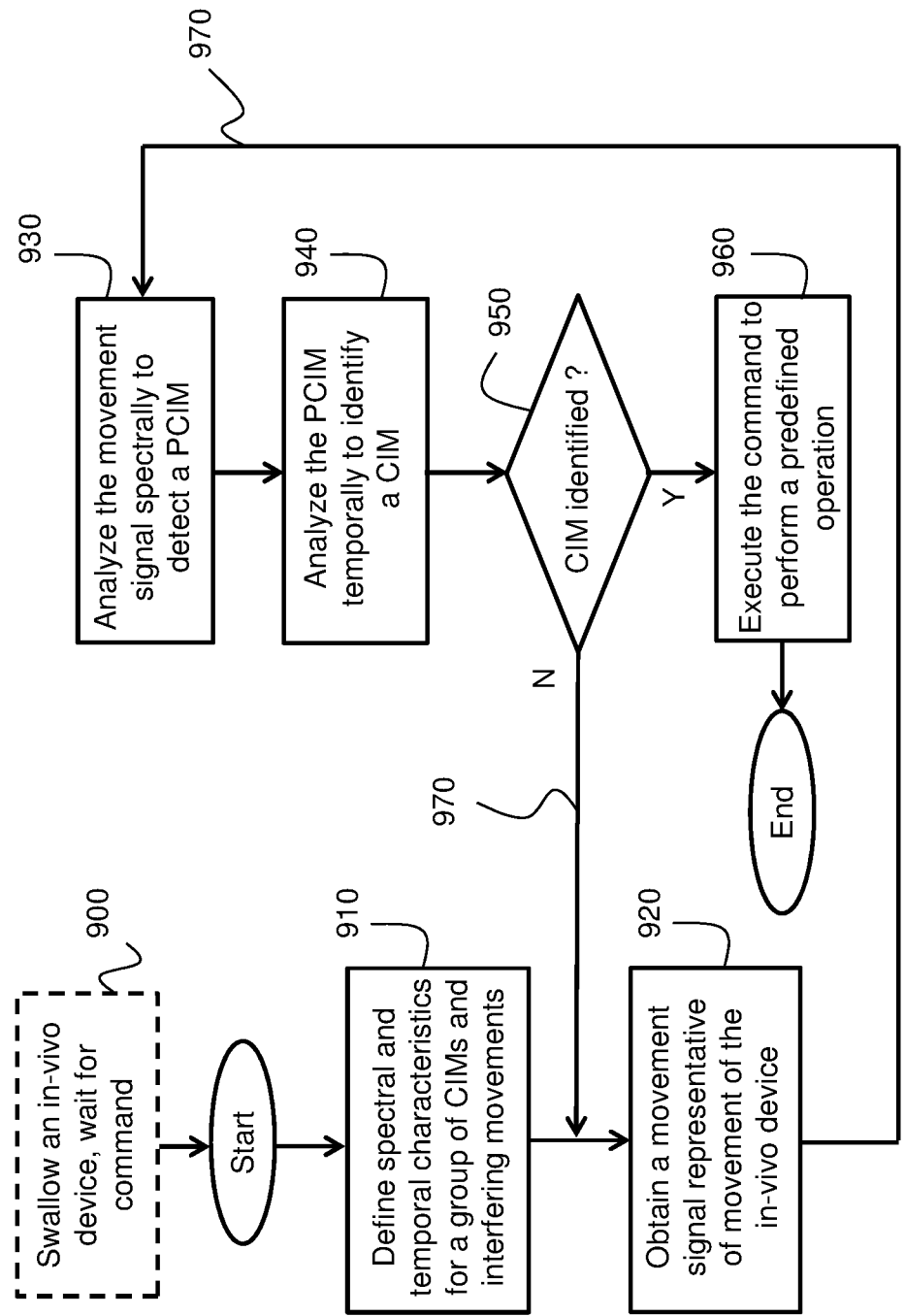
FIG. 9 shows a method for detecting a command-invoking movement (CIM) of an in-vivo device (e.g., the device of FIG. 8) according to an embodiment of the present invention.

FIG. 9 shows a method for detecting a command invoking movement of an in-vivo sensing device (e.g., device 810 of FIG. 8) according to an example embodiment of the present invention. At step 900, a swallowable in-vivo device (e.g., in-vivo device 810) is swallowed and its movement may continuously, intermittently or occasionally be monitored relative to a non-stationary three-dimensional reference frame. At step 910, a group of fiducial CIMs and a group of interference movements are predefined, and spectral and temporal characteristics that characterize each movement in each group may be predefined and stored, for example, in storage unit 822. Spectral and temporal characteristics of fiducial CIMs and interference movements may be defined and stored (e.g., in storage unit 822 prior to the activation or swallowing of the in-vivo device, e.g., they may be stored at the time of manufacture. Storage unit 822 may also store time specifics defining time templates against which movement events may be compared or analyzed in order to corroborate or refute an initial determination, or assumption, that a device movement (PCIM), which frequency-wise resembles a fiducial CIM, is a CIM.

At step 920, a movement signal representative of movement of the in-vivo device may be obtained, for example, by using one or more movement sensors, for example accelerometers that are mentioned in connection with acceleration sensor(s) unit 410. (Other sensors facilitating detection of movement may be used; e.g., magnetometer(s), gyroscope(s), etc.) The accelerometers (or another sensor) may be used to detect a series of movements, or movement events, of the in-vivo device in the non-stationary three-dimensional reference frame. A determination whether a particular movement event, which may be detected in the movement signal is, or is not, a CIM may include spectrally analyzing the particular movement event vis-a-vis fiducial CIMs to determine whether the particular movement is a potential CIM (PCIM), as per step 930, and performing temporal analysis, as per step 940, to corroborate, or refute, the determination.

At step 930 the movement signal may be analyzed spectrally (e.g., by a FAU similar to FAU 500) vis-a-vis fiducial CIMs to detect one or more PCIMs, with each command-invoking movement is associated a command. The spectral analysis of the movement signal may include comparing spectral features of the detected movement to spectral features of fiducial CIMs. The movement signal, or an interim processing version thereof, may be analyzed spectrally and/or temporally one or more times, or iteratively or repeatedly, and at any order (e.g., first spectrally and then temporally, or vice versa) before the final decision is made. (A PCIM is a movement that resembles a CIM but it may not be a CIM despite the resemblance. For example, a PCIM may be a movement event that is part of a series of interference movements.) However, a final decision regarding classification of this movement event as a CIM or an interference movement (for example) may be made using time analysis, as described and demonstrated herein. (The movement signal may be analyzed temporally and/or spectrally vis-a-vis the interference movements before it is spectrally analyzed vis-a-vis the fiducial CIMs, in order to remove (filter out)

interference movements from the movement signal and, thereby, simplify detection of PCIMs in the movement signal.)

A determination whether a particular movement event (e.g., PCIM) in a series of movements is, or is not, a CIM (e.g., classifying the particular movement event, or PCIM, as a CIM or as an interference movement) may further include temporally analyzing (e.g., by a TAU similar to TAU 620 or TAU 700) a series of movement events (e.g., PCIMs), including the particular movement event (PCIM), as a whole (e.g., en masse) in order to determine whether the particular movement event (PCIM) is, or is not, a (genuine) CIM, as per step 940. Step 940 may include temporally analyzing a particular one of the one or more PCIMs vis-a-vis one or more interference movements to determine whether the particular PCIM is a CIM or, for example, an interference movement.

In step 950 the particular movement event, or PCIM may be classified. If it is determined that the PCIM is a (genuine) CIM (shown as "Y" at step 950), then, at step 960, the predetermined command associated with the particular movement event (the command associated with the detected CIM), may be executed (e.g., by a controller similar to controller 490 or controller 818) in order to perform a predefined operation or operations. However, if it is determined that the PCIM is not a CIM (shown as "N" at step 950), the controller may refrain from executing any predetermined command associated with any CIM, and loop 970 may be repeated or iterated as long as the movement signal is continued to be produced and monitored, in order to detect another movement event, and to determine whether each detected movement event represents, or is related to, elicited by or derived from a CIM or from an interference movement.

Filtering out an interference movement from a movement signal may include using information indicative of a location and/or an orientation of the in-vivo device for which movement is to be detected. Selection of a fiducial CIM for use may depend on the location of the in-vivo device: different sets of fiducial CIMs may be used for different locations of the device. (Different sets of fiducial CIMs may include common fiducial CIM(s). A set of fiducial CIMs may include one CIM.) Filtering out an interference movement from a movement signal may include analyzing the movement signal by iteratively performing spectral analysis and temporal analysis. A movement of the in-vivo device may be classified as a command-invoking movement or as an interference movement depending (e.g., based) on the location and/or orientation of the in-vivo device relative to any of a non-stationary three-dimensional reference frame (e.g., the gastrointestinal tract or a portion thereof containing the in-vivo device).

According to embodiments of the present invention, a printed circuit board (PCB) for enabling (e.g., an in-vivo device) detection of CIMs is also provided, which PCB may include: a primary branch comprising installation units, a processor mounted on a first installation unit, and a first movement sensor mounted on a second installation unit; and a first secondary branch comprising installation units and a second movement sensor mounted on an installation unit of the first secondary branch. The first secondary branch may be connected, for example perpendicularly, to the primary branch via a common installation unit. The PCB may include a second secondary branch including installation units and an imaging sensor that may be mounted on an installation unit of the second secondary branch. The second secondary branch may be connected to the primary branch via a common installation unit. The PCB may be foldable so that the installation units of the primary branch and the installation units of the two secondary branches are stacked along a common lengthwise axis. The processor may be configured to for example detect a series of movements of the in-vivo sensing device from data obtained/originating from the first movement sensor and/or the second movement sensor; spectrally analyze the series of movements vis-a-vis fiducial CIMs, where each fiducial CIM represents a device movement invoking an associated command, to detect a potential CIM, and temporally analyze the series of movements to determine whether the potential CIM is, or is not, a genuine CIM. The processor may further be configured to execute a command associated with the potential CIM if, based on the temporal analysis, the potential CIM is determined (e.g., by the processor) to be a genuine CIM. The processor may perform other functions for example as described herein. An example PCB implementing embodiments of the methods disclosed herein is depicted in FIGS. 10A-10C, which are described below.

FIGS. 10A and 10B depict a spread out PCB 1000 according to an example embodiment. (FIG. 10B is a flip over depiction of the PCB of FIG. 10A.) FIG. 10C is a three-dimensional depiction of PCB 1000 of FIGS. 10A-10B. PCB 1000, which is flexible, may include a primary PCB branch and two secondary PCB branches that are connected to primary PCB branch 1010. (The primary PCB branch and the secondary PCB branches are respectively shown at 10, 1020 and 1030 in FIG. 10B.) Secondary PCB branches 1020 and 1030 are perpendicular to primary PCB branch 1010.

Primary PCB branch 1010 may include PCB installation units 1012, 1014, 1016 and 1018, a flexible connection unit 1013 that interconnects PCB installation units 1012 and 1014, a flexible connection unit 1015 that interconnects PCB installation units 1014 and 1016, and a flexible connection unit 1017 that interconnects PCB installation units 1016 and 1018. A first secondary PCB branch 1020 may include PCB installation units 1014 and 1024 and a flexible connection unit 1022 that interconnects them. A second secondary PCB branch 1030 may include PCB installation units 1016 and 1036 and a flexible connection unit 1032 that interconnects them. PCB installation unit 1014 is common to primary PCB branch 1010 and to secondary branch 1020, and PCB installation unit 1016 is common to primary PCB branch 1010 and to secondary branch 1030. The common PCB installation units 1014 and 1016 may be regarded as 'PCB hubs' via which the various branches of PCB 1000 are mechanically and functionally connected.

Each PCB installation unit of PCB 1000 may include (e.g. have mounted thereon) an optical and/or an electrical (or electromechanical) component of the in-vivo device. For example, PCB installation unit 1024 may include an imager 1026 and for example four illumination sources (e.g., four LEDs, one of which is shown at 1028). (Imager 1026 and the illumination sources may respectively be similar to imager 812 and light source 814 of FIG. 8.) PCB installation unit 1018 may include a sensor module 1040 that may be or include three accelerometers to sense movement of an in-vivo sensing device in three directions. PCB installation unit 1036 may include a sensor module 1050 that may be or include three magnetometers to facilitate sensing of the location and orientation of the in-vivo device. PCB installation unit 1012 may include a radio frequency ("RF") communication antenna 1003; PCB installation unit 1014 may include a RF transmitter 1005 and PCB installation unit 1016 may include a processor 1007 for processing acceleration data and/or magnetic data and/or gyroscopic data (depending on the implementation). Other PCB installation units may include, for example, a crystal oscillator, a remotely operated "on/off" switch to switch an in-vivo sensing device on and off, a battery contact (e.g., in the form of a spring coil) to contact a positive or negative pole of a battery, a data storage unit to store en executable instruction code for implementing the methods disclosed herein, etc. By way of example, PCB installation units 1024, 1014, 1016 and 1018 may respectively include spring coils 1060, 1070, 1080 and 1090.

Sensor module 1040 may preferably be located at (or approximately at) the center of mass of PCB 1000 in order to minimize detection of mechanical moments due to rotational movement of the folded PCB (see FIG. 10C) relative to the center of mass of PCB 1000. In FIG. 10C, the space between spring coils 1060 and 1090 is used to accommodate one or more batteries, and the space between spring coils 1070 and 1080 is also used to accommodate one or more batteries. Due to their considerable weight and location, when the batteries are put in place, the center of mass of the PCB (with the batteries and mounted components) is between PCB installation units 1016 and 1018. As explained herein, sensor module 1040 is to be interposed between the two batteries, hence the location of sensor module 1040 between PCB installation units 1016 and 1018. Sensor module 1050, on the other hand, is to be preferably located as far from the batteries as possible (e.g., furthest, or distanced away, from the center of mass of the in-vivo device) in order to minimize the distortion effect of the batteries on the magnetic field that is to be sensed by the magnetometer(s) of component 1050. Therefore, sensor module 1050 is mounted on PCB installation unit 1036 which, after folding of PCB 100, is the farthest PCB installation unit from the batteries.

FIGS. 10A-10C depict an example configuration where the acceleration sensor(s) and the magnetometer are physically separated (e.g., the accelerometer(s) and the magnetometer(s) are mounted on different installation units) for ease of operation and processing. However, other configurations may be used, where the two functionalities are integrated into one device, and the device may be mounted on installation unit 1018 or on installation unit 1036. For example, if a maximum mechanical moment expected to be applied to an accelerometer(s) is weak, the accelerometer can be distanced away from the center of mass of folded PCB 1000 (e.g., it can be mounted on installation unit 1036, for example together with the magnetometer(s) 1050). If the distortion in the magnetic field due to, for example, the batteries is small, or if the magnetic field is mathematically restorable from the distorted magnetic field, the magnetometer(s) can be positioned at (or near) the center of mass of folded PCB 100 (e.g., it can be mounted on installation unit 1018, for example together with accelerometer(s) 1040).

The FXOS8700CQ sensor provided by Freescale Semiconductor features a small form factor (3 mm by 3 mm by 1.2 mm), low-power, device integrating linear accelerometer and magnetometer sensors. Components 1040 and/or 1050 may be or include such a sensor or another suitable sensor. If component 1040 is to function as an accelerometer, the magnetometer functionality of the FXOS8700CQ device may be disabled, and if component 1050 is to function as a magnetometer, the accelerometer functionality of the FXOS8700CQ device may be disabled. The BMX055 sensor provided by BOSCH features a small form factor device integrating triaxial accelerometer, triaxial gyroscope and triaxial geomagnetic sensor, which makes it a candidate for sensor modules 1040 and 1050. (Other off the shelf sensors, and devices that may be specifically devised, may be used as sensor modules 1040 and 1050.)

PCB 1000 may be fully flexible or partly rigid and partly flexible (e.g., it may be rigid-flex, which may for example include flexible portions and rigid portions). For example, each of PCB installation units 1012, 1014, 1016, 1018, 1024 and 1036, may be rigid or flexible. Flexible connection units 1013, 1015, 1017, 1022 and 1032 enable folding PCB 1000 into a cylindrically shape object. PCB 1000 of FIGS. 10A-10B is shown in FIG. 10C folded to a three-dimensional object 1004 whose general shape resembles a cylinder having a lengthwise axis 1002. (Flexible PCB 1000 is foldable so that the six installation units are stacked along common lengthwise axis 1002.) When PCB 100 is folded, all of its PCB installation units are parallel and perpendicular to lengthwise axis 1002. By imparting to PCB 1000 a shape of a cylinder (e.g., after folding the PCB), PCB 1000 may snugly fit into a cylindrical housing of a capsule-like in-vivo sensing device. As illustrated in FIGS. 10A-10C, the accelerometer(s) (component 1040) is mounted on primary PCB branch 1010 and the magnetometer(s) (component 1050) is mounted on secondary PCB branch 1030. As described above, this PCB configuration 'puts' the accelerometer(s), after the PCB is folded, at or near the center of mass of the PCB, and distances the magnetometer(s) as far as possible from the batteries.

Each installation unit and connection portion of PCB 1000 may have n layers (n=1, 2, 3, . . . ,), and circuit components, which may be mounted on the various layers, may be electrically interconnected through for example micro vias.

A flexible circuit board 1000 may have a primary PCB branch 1010 and two secondary PCB branches (branches 1020 and 1030) that are perpendicular to primary PCB branch 1010. According to this configuration, accelerometer 1040 may be mounted on primary PCB branch 1010 and magnetometer 1050 may be mounted on one of the two secondary PCB branches (e.g., on secondary PCB branch 1020).

Flexible circuit board 1000 has a component side, which is shown in FIG. 10A, and a second side, which is shown in FIG. 10B. The circuit board may include: a first installation unit 1012 that has a first side on which RF antenna 1003 is disposed; a second installation unit 1014 that has a first side on which RF transmitter 1005 is disposed, and a second side on which a battery contact (spring coil) 1070 is mounted, the second installation unit (1014) is connected to the first installation unit (1012) by flexible connection unit 1013; a third installation unit (1016) having a first side on which processor 1005 is disposed, and a second side on which a battery contact (spring coil) 1080 is mounted, the third installation unit (1016) is connected to the second installation unit (1014) by flexible connection unit 1015; a fourth installation unit (1018) having a first side on which an accelerometer 1040, or magnetometer 1050, or both accelerometer 1040 and magnetometer 1050 is/are disposed, and a second side on which a battery contact (spring coil) 1090 is mounted, the fourth installation unit (1018) is connected to the third installation unit (1016) by flexible connection unit 1017; a fifth installation unit (1024) having a first side on which imager 1026 is disposed, and a second side on which a battery contact (spring coil) 1060 is mounted, the fifth installation unit (1024) is connected to the second installation unit (1014) by flexible connection unit 1022; and a sixth installation unit (1036) having a first side on which an accelerometer 1040, or magnetometer 1050, or both accelerometer 1040 and magnetometer 1050 is/are disposed, the sixth installation unit (1036) is connected to the third installation unit (1016) by flexible connection unit 1032.

According to an example embodiment, flexible PCB 100 is configured such that after it is folded, the first, second, third, fourth, fifth and sixth flexible installation units are stacked along a common lengthwise axis (e.g., axis 1002) and form an object whose shape is generally cylindrical. According to an example embodiment, processor 1007 may be configured to process data representing acceleration and/or magnetic field and/or gyroscopic information and/or altimeter information (if an altimeter is incorporated into the in-vivo sensing device) in order to detect movement and/or location and/or orientation of an in-vivo sensing device, and to execute a program that implements the methods disclosed herein in order to determine, among other things, whether a detected movement is a CIM, or not. For example, processor 1007 may be configured to detect a movement of the in-vivo sensing device by using information that is obtained from any of the sensors mounted on PCB 100, and to determine whether the detected movement is a CIM, or not, and to execute a predetermined command if the detected movement is a CIM, or refrain from executing a CIM-related command if the movement is not a CIM.

Embodiments of the invention may include an article such as a computer or processor readable non-transitory storage medium, such as for example a memory, a disk drive, or a USB flash memory device encoding, including or storing instructions, e.g., computer-executable instructions, which when executed by a processor or controller, cause the processor or controller to carry out methods disclosed herein. The various processors or controllers discussed herein may in some embodiments be configured to carry out methods according to embodiments of the invention by for example being connected to a memory storing software or instructions which when executed cause the processor to carry out such methods.

The articles "a" and "an" are used herein to refer to one or to more than one (e.g., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. Features (e.g., frequency features, temporal features) of certain embodiments may be used with other embodiments shown herein. The present disclosure is relevant to various types of in-vivo devices (e.g., in-vivo devices with one or more imagers, in-vivo devices with no imagers at all, etc.). Hence the scope of the claims that follow is not limited by the disclosure herein.

The invention claimed is:

1. A method for executing a command by a swallowable in-vivo device configured to move relative to a non-stationary three-dimensional reference frame and comprising a movement sensor, the method comprising:

spectrally analyzing, using a controller, a movement signal outputted from the movement sensor vis-a-vis fiducial command-invoking movements to detect one or more potential command-invoking movements, wherein each command-invoking movement is associated with a command;

temporally analyzing, using the controller, a particular one of the one or more potential command-invoking movements vis-a-vis one or more interference movements to classify the particular potential command-invoking movement as a command-invoking movement or as an interference movement;

if the particular potential command-invoking movement is classified as a command-invoking movement, executing, using the controller, a command associated with the command-invoking movement; and if the particular potential command-invoking movement is classified as an interference movement, refraining from executing, using the controller, any command that is associated with any command-invoking movement.

2. The method as in claim 1, comprising filtering out an interference movement from the movement signal prior to the spectral analysis of the movement signal.

3. The method as in claim 2, wherein filtering out the interference movement from the movement signal comprises analyzing the movement signal spectrally, or temporally, or both spectrally and temporally vis-a-vis spectral characteristics, or temporal characteristics, or both spectral and temporal characteristics of the interference movement.

4. The method as in claim 2, wherein filtering out the interference movement from the movement signal comprises any of: (i) analyzing the movement signal spectrally and then temporally, or temporally and then spectrally, using the pertinent spectral and temporal characteristics; (ii) using information indicative of a location, or an orientation, or both a location and an orientation of the in-vivo device; and (iii) analyzing the movement signal by iteratively performing spectral analysis and temporal analysis.

5. The method as in claim 1, wherein classifying a potential command invoking movement as a command-invoking movement or as an interference movement depends on a location, or orientation, or both location and orientation of the in-vivo device relative to the non-stationary three-dimensional reference frame.

6. The method as in claim 1, wherein determining whether the particular potential command-invoking movement is a command-invoking movement comprises analyzing the movement signal spectrally and then temporally, or temporally and then spectrally.

7. The method as in claim 1, wherein determining whether the particular potential command-invoking movement is a command-invoking movement comprises analyzing the movement signal by iteratively performing spectral analysis and temporal analysis.

8. The method as in claim 1, wherein the non-stationary three-dimensional reference frame is the gastrointestinal tract or a portion thereof containing the in-vivo device.

9. The method as in claim 1, wherein a command associated with a command-invoking movement is selected from the group consisting of: command to change an image capturing rate of a camera of the in-vivo device, a command to change an operation mode or state of the in-vivo device and a command to transmit a message to a receiver external to the in-vivo device.

10. The method as in claim 1, wherein command-invoking movement is selected from a group consisting of: movement due to contraction of the small bowel, movement due to contraction of the colon, movement due to contraction of the stomach, and movement due to intestine constipation, wherein an interference movement is a movement selected from a group consisting of: movement due to human body gestures, movement due to human walking/running, movement due to respiration, movement due to coughing, movement due to finger tapping, and movement due to heart beating.

11. The method as in claim 1, wherein the movement signal comprises three movement signals corresponding to movement in three directions.

12. The method as in claim 11, comprising analyzing the three movement signals to detect a command-invoking movement when the in-vivo device is in the stomach, and analyzing one movement signal to detect a command-invoking movement when the in-vivo device is in the small bowel.

13. A method for executing a command by a swallowable in-vivo device configured to move to a non-stationary three-dimensional reference frame and comprising a movement sensor, the method comprising:

spectrally analyzing, using a controller, a movement signal outputted from the movement sensor vis-a-vis fiducial command-invoking movements to detect a potential command-invoking movement associated with a command;

temporally analyzing, using the controller, the potential command-invoking movements vis-a-vis interference movements to classify the particular potential command-invoking movement as a command-invoking movement or as an interference movement; and executing the command, using the controller, if the potential command-invoking movement is classified as the command-invoking movement, and refraining from executing the command, using the controller, if the potential command-invoking movement is classified as the interference movement.

14. A swallowable in-vivo device comprising:

a memory device to store (i) spectral characteristics and temporal characteristics of fiducial command-invoking movements respectively representing device movements invoking commands, and (ii) spectral characteristics and temporal characteristics of interference movements;

a movement sensor to output a movement signal representing movement of the in-vivo device; and a controller configured to,
(i) spectrally analyze the movement signal vis-a-vis fiducial command-invoking movements to detect one or more potential command-invoking movements, with each command-invoking movement is associated a command;
(ii) temporally analyze a particular one of the one or more potential command-invoking movements vis-a-vis one or more interference movements to determine whether the particular potential command-invoking movement is a command-invoking movement or an interference movement; and
(iii) execute a command associated with the command-invoking movement or refrain from executing any command-invoking movement related command based on the results of the spectral analysis and temporal analysis.

15. The swallowable in-vivo device as in claim 14, wherein the movement sensor comprises a sensor selected from a group consisting of accelerometer, magnetometer and gyroscope.

16. The swallowable in-vivo device as in claim 14, further comprising a matched filters array module configured to detect a command-invoking movement from the movement signal relative to a non-stationary three-dimensional reference frame.

17. The swallowable in-vivo device as in claim 16, wherein the matched filters array module comprises a band pass filter for each command-invoking movement or for a group of command-invoking movements.

18. The swallowable in-vivo device as in claim 14, wherein the movement sensor comprises an accelerometer whose sensing direction coincides with a longitudinal axis of the in-vivo device.

* * * * *